United States Patent [19]
Schohe-Loop et al.

[11] Patent Number: 5,760,230
[45] Date of Patent: Jun. 2, 1998

[54] 4, 4'-BRIDGED BIS-2, 4-DIAMINOQUINAZOLINES

[75] Inventors: Rudolf Schohe-Loop, Wuppertal; Peter-Rudolf Seidel, Köln; William Bullock, Wuppertal; Achim Feurer, Odenthal; Hans-Georg Lerchen, Köln; Georg Terstappen, Düsseldorf; Joachim Schuhmacher, Wuppertal; Franz-Josef van der Staay, Lohmar/Wahlscheid; Bernard Schmidt, Lindlar, all of Germany; Richard J. Fanelli, Madison, Conn.; Jane C. Chisholm, Clinton, Conn.; Richard T. McCarthy, Madison, Conn.

[73] Assignee: Bayer Aktiengesellschaft, Leverkusen, Germany

[21] Appl. No.: 728,927

[22] Filed: Oct. 11, 1996

[51] Int. Cl.[6] .................... C07D 239/00; A61K 31/505
[52] U.S. Cl. ................................... 544/284; 514/260
[58] Field of Search ........................ 544/284; 514/260

[56] References Cited

FOREIGN PATENT DOCUMENTS

| 188094 | 7/1986 | European Pat. Off. ...... C07D 471/04 |
| 9304048 | 3/1993 | WIPO ........................... C07D 241/26 |

OTHER PUBLICATIONS

Yu et al., (CA AN 1993:551627, Bioorg. Med. Chem. Lett. (1992), 2(9), 1121–6).

Ding et al., (AN 1985:160042, Shanghai Inst. Pharm. Ind., Shanghai, Peop. Rep. China).

Hynes et al., (AN 1973:52530, J. Med. Chem. (1972), 15(12), 1332–3).

Zhang et al., (AN 1989:33336, Yiyao Gongye (1988), 19(9), 396–400).

Haberman et al., "Bee Venom Neurotoxin (Apamin): Iodine Labeling and Characterization Binding Sites," Eur.J.Biochem. 94, 355–364 (1979).

Mourre et al., "Quantitative Autoradiographic Mapping in Rat Brain of the Receptor of Apamin, a Polypeptide Toxin Specific for One Class of $Ca^{2+}$–dependent $K^+$ Channels," Brain Research, 382, 239–249 (1986).

Heurteaux et al., "Memory processing and apamin induce immediate early gene expression in mouse brain," Molecular Brain Research, 3, 17–22 (1993).

Messier et al., "Effect of apamin, a toxin that inhibits $Ca^{2+}$–dependent $K^+$ channels, on learning and memory processes," Brain Research, 551, 322–326 (1991).

Behrens et al., "Possible Role of Apamin–Sensitive $K^+$ Channels in Myotonic Dystrophy," Muscle & Nerve, 1264–1270 (1994).

"Depression: a new animal model sensitive to antidepressant treatments," Nature, 266, 730–732 (1977).

Morris, "Developments of a water–maze procedure for studying spatial learning in the rat," Journal o Neuroscience Methods, 11, 47–60 (1984).

*Primary Examiner*—Jose G. Dees
*Assistant Examiner*—Sabiha N. Qazi
*Attorney, Agent, or Firm*—Sprung Kramer Schaeffer & Briscoe

[57] ABSTRACT

4,4'-Bridged bis-2,4-diaminoquinazolines of the general formula (I)

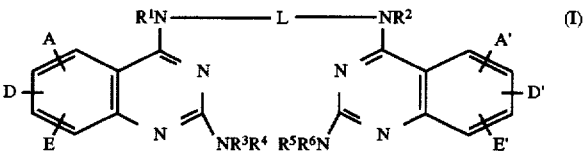

processes for their preparation and use as agents acting on the potassium channels of the brain.

7 Claims, No Drawings

4,4'-BRIDGED BIS-2,4-DIAMINOQUINAZOLINES

Novel 4,4-bridged bis-2,4-diaminoquinazolines

The present invention relates to novel 4,4'-bridged bis-2,4-diaminoquinazolines, to processes for their preparation and to their use in drugs, especially as agents acting on the brain.

4,4'-Diamino-2,2'-piperazinyl-bridged, alkoxy-substituted bisquinazolines and their peripheral action, especially as antihypertensives, are known [cf. EP 188 094]. The present invention relates to novel 4,4'-bridged bis-2,4-diaminoquinazolines of the general formula (I)

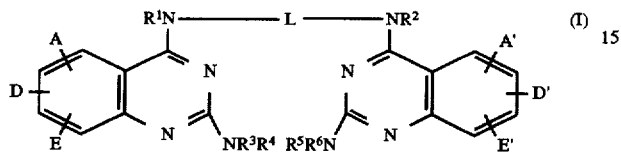

in which

A, A', D, D', E and E' are identical or different and are hydrogen, halogen, hydroxyl, nitro, trifluoromethyl, trifluoromethoxy or linear or branched alkyl or alkoxy, each of which has up to 6 carbon atoms, L is a linear or branched alkylene chain having up to 20 carbon atoms which is optionally interrupted by an oxygen or sulfur atom or by a group of the formula —NR$^7$, wherein R$^7$ is hydrogen or linear or branched alkyl having up to 4 carbon atoms, and where the alkylene chain is optionally substituted by up to 3 identical or different substituents selected from hydroxyl, linear or branched alkoxy having up to 5 carbon atoms, aryl or aralkoxy, each of which has up to 10 carbon atoms, and a 5- to 7-membered aromatic, optionally benzo-fused heterocycle having up to 3 heteroatoms from the group comprising S, N and/or O, it being possible for the rings in turn to be substituted by halogen, hydroxyl, cyano, linear or branched alkoxy having up to 6 carbon atoms, or a radical of the formula —(NH)$_a$—CONR$^8$R$^9$, wherein R$^8$ and R$^9$ are identical or different and are hydrogen or linear or branched alkyl having up to 6 carbon atoms, and a is the number 0 or 1, or L is a radical of the formula —(CH$_2$)$_b$—T—(CH$_2$)$_c$, wherein b and c are identical or different and are the number 0, 1, 2, 3, 4 or 5, and T is cycloalkyl having 3 to 6 carbon atoms, aryl having 6 to 10 carbon atoms or a 3- to 8-membered, saturated or unsaturated, optionally benzo-fused and/or heterocyclically or carbocyclically bridged heterocycle having up to 3 heteroatoms from the group comprising S, N and/or O, wherein all the ring systems are optionally substituted by up to 3 identical or different substituents selected from halogen, cyano, hydroxyl, nitro, carboxyl, linear or branched alkyl, alkoxycarbonyl or alkoxy, each of which has up to 9 carbon atoms, and a radical of the formula —CO—NR$^{10}$R$^{11}$, wherein R$^{10}$ and R$^{11}$ are as defined above for R$^8$ and R$^9$ and are identical thereto or different therefrom, R$^1$ and R$^2$ are identical or different and are hydrogen, phenyl or linear or branched alkyl having up to 6 carbon atoms which is optionally substituted by hydroxyl, halogen or a radical of the formula —NR$^{12}$R$^{13}$, wherein R$^{12}$ and R$^{13}$ are identical or different and are as defined above for R$^8$ and R$^9$, or R$^1$, R$^2$ and L, together with the two nitrogen atoms, form a 5- to 8-membered, saturated, partially unsaturated or aromatic heterocycle which is optionally benzo-fused and/or substituted by hydroxyl, carboxyl, linear or branched acyl or alkoxycarbonyl, each of which has up to 6 carbon atoms, phenyl or linear or branched alkyl having up to 6 carbon atoms, which in turn is substituted by hydroxyl, carboxyl, ureido, linear or branched alkoxy, acylamino or alkoxycarbonyl, each of which has up to 5 carbon atoms, or a group of the formula —(CO)$_d$—NR$^{14}$R$^{15}$, wherein d is the number 0 or 1, and R$^{14}$ and R$^{15}$ are identical or different and are as defined above for R$^8$ and R$^9$, and/or the heterocycle is optionally substituted by a radical of the formula —(CO)$_e$—NR$^{16}$R$^{17}$, wherein e is as defined above for d and is identical thereto or different therefrom, and R$^{16}$ and R$^{17}$ are identical or different and are as defined above for R$^8$ and R$^9$, or, in the case where b is the number 0 and c is as defined above, or c is the number 0 and b is as defined above, T and R$^1$ or, respectively, T and R$^2$, in each case together with the nitrogen atom, form a 3- to 8-membered, optionally benzo-fused and/or heterocyclically or carbocyclically bridged, saturated heterocycle having up to 2 heteroatoms from the group comprising S, N and/or O, and R$^3$, R$^4$, R$^5$ and R$^6$, are identical or different and are hydrogen, phenyl or linear or branched alkyl having up to 8 carbon atoms which is optionally substituted by hydroxyl, halogen or a radical of the formula —NR$^{18}$R$^{19}$, wherein R$^{18}$ and R$^{19}$ are identical or different and are as defined above for R$^8$ and R$^9$, or R$^3$ and R$^4$ and/or R$^5$ and R$^6$, in each case together with the nitrogen atom, form a 5- to 7-membered saturated heterocycle which can optionally contain up to 2 further heteroatoms from the group comprising S and O, or a radical of the formula —NR$^{20}$, wherein R$^{20}$ is as defined above for R$^7$ and is identical thereto or different therefrom, and their salts.

Biocompatible salts are preferred within the framework of the present invention. Biocompatible salts of the novel 4,4'-bridged bis-2,4-diaminoquinazolines can be salts of the substances according to the invention with mineral acids, carboxylic acids or sulfonic acids. Examples of particularly preferred salts are those with hydrochloric acid, hydrobromic acid, sulfuric acid, phosphoric acid, methanesulfonic acid, ethanesulfonic acid, toluenesulfonic acid, benzenesulfonic acid, naphthalenedisulfonic acid, acetic acid, propionic acid, lactic acid, tartaric acid, citric acid, fumaric acid, maleic acid or benzoic acid.

The compounds according to the invention can be present in different stereo-isomeric forms within the framework of the present invention. The compounds according to the invention exist in stereoisomeric forms which either behave as image and mirror image (enantiomers) or do not behave as image and mirror image (diastereoisomers). The invention relates both to the antipodes and to the racemic forms and the diastereoisomeric mixtures. The racemic forms and the diastereoisomers can be resolved in known manner into the stereoisomerically pure components.

Within the framework of the invention, a heterocycle is generally a saturated or unsaturated 5- to 8-membered, preferably 6- or 7-membered heterocycle which can contain up to 3 heteroatoms from the group comprising S, N and/or O. Examples which may be mentioned are pyridyl, thienyl, furyl, pyrrolyl, thiazolyl, oxazolyl, imidazolyl, morpholinyl or piperidyl. Pyridyl and thienyl are preferred.

A 3- to 8-membered saturated heterocycle bonded via the nitrogen atom, which can also contain up to 2 oxygen, sulfur and/or nitrogen atoms as heteroatoms, is generally azetidinyl, piperidyl, morpholinyl, piperazinyl, pyrrolidinyl, 1,4-diazacycloheptyl or [1,5]-diazoxanyl. 7- and 8-membered rings with one oxygen atom and/or up to 2 nitrogen atoms, for example 1,4-diazacycloheptyl or [1,5]-diazoxanyl, are preferred. 1,4-Diazacycloheptyl and [1,5]-diazoxanyl are particularly preferred.

Preferred compounds of the general formula (I) are those in which

A, A', D, D', E and E' are identical or different and are hydrogen, fluorine, chlorine, bromine, hydroxyl, nitro, trifluoromethyl, trifluoromethoxy or linear or branched alkyl or alkoxy, each of which has up to 4 carbon atoms, L is a linear or branched alkylene chain having, up to 15 carbon atoms which is optionally interrupted by an oxygen or sulfur atom or by a group of the formula $-NR^7$, wherein $R^7$ is hydrogen or linear or branched alkyl having up to 3 carbon atoms, and where the alkylene chain is optionally substituted by up to 2 identical or different substituents selected from hydroxyl, linear or branched alkoxy having up to 4 carbon atoms, phenyl, benzyloxy, phenoxy, pyridyl, pyrimidyl, pyridazinyl, quinolyl and isoquinolyl, it being possible for the rings in turn to be substituted by fluorine, chlorine, bromine, hydroxyl, cyano, linear or branched alkoxy having up to 4 carbon atoms, or a radical of the formula $-(NH)_a$-$CONR^8R^9$, wherein $R^8$ and $R^9$ are identical or different and are hydrogen or linear or branched alkyl having up to 4 carbon atoms, and a is the number 0 or 1, or a radical of the formula $-(CH_2)_b-T-(CH_2)_c$- wherein b and c are identical or different and are the number 0, 1, 2, 3 or 4, and T is cyclopropyl, cyclobutyl, cyclopentyl, cyclohexyl, cycloheptyl, phenyl, naphthyl, pyridyl, quinolyl, isoquinolyl, morpholinyl or piperidinyl which is optionally substituted by up to 2 identical or different substituents selected from fluorine, chlorine, bromine, cyano, hydroxyl, carboxyl, linear or branched alkyl, alkoxycarbonyl or alkoxy, each of which has up to 7 carbon atoms, and a radical of the formula $-CO-NH_2$, $R^1$ and $R^2$ are identical or different and are hydrogen or linear or branched alkyl having up to 3 carbon atoms which is optionally substituted by hydroyl, fluorine or a radical of the formula $-NR^{12}R^{13}$, wherein $R^{12}$ and $R^{13}$ are identical or different and are hydrogen or linear or branched alkyl having up to 5 carbon atoms, or $R^1$, $R^2$ and L, together with the two nitrogen atoms, form a piperazinyl, 1,4-diazacycloheptyl or [1,5]-diazoxanyl ring which is optionally substituted by hydroxyl, carboxyl, linear or branched acyl or alkoxycarbonyl, each of which has up to 5 carbon atoms, phenyl or linear or branched alkyl having up to 5 carbon atoms, which can in turn be substituted by hydroxyl, carboxyl, ureido, linear or branched alkoxy, acylamino or alkoxycarbonyl, each of which has up to 4 carbon atoms, or a group of the formula $-(CO)_d-NR^{14}R^{15}$, wherein d is the number 0 or 1, and $R^{14}$ and $R^{15}$ are identical or different and are hydrogen or linear or branched alkyl having up to 4 carbon atoms, and/or the heterocycles are optionally substituted by a radical of the formula $-(CO)_e-NR^{16}R^{17}$, wherein e is as defined above for d and is identical thereto or different therefrom, and $R^{16}$ and $R^{17}$ are identical or different and are as defined above for $R^{14}$ and $R^{15}$, or, in the case where b is the number 0 and c is as defined above, or c is the number 0 and b is as defined above, T and $R^1$ or, respectively, T and $R^2$, in each case together with the nitrogen atom, form a piperidine, morpholine, pyrrolidine or 4-azatricyclo[5.2.2.0]-2,6-undecenyl ring, and $R^3$, $R^4$, $R^5$ and $R^6$ are identical or different and are hydrogen or linear or branched alkyl having up to 7 carbon atoms which is optionally substituted by hydroxyl, fluorine or a radical of the formula $-NR^{18}R^{19}$, wherein $R^{18}$ and $R^{19}$ are identical or different and are as defined above for $R^{14}$ and $R^{15}$, or $R^3$ and $R^4$ and/or $R^5$ and $R^6$, in each case together with the nitrogen atom, form a morpholine, piperazinyl, piperidinyl or pyrrolidinyl ring and their salts.

Particularly preferred compounds of the general formula (I) are those in which

A, A', D, D', E and E' are identical or different and are hydrogen, fluorine, chlorine, nitro, trifluoromethyl, trifluoromethoxy or linear or branched alkyl having up to 3 carbon atoms, L is a linear or branched alkylene chain having up to 10 carbon atoms which is optionally interrupted by an oxygen or sulfur atom or by a group of the formula $-NR^7$, wherein R[7] is hydrogen or linear or branched alkyl having up to 3 carbon atoms, and where the alkylene chain is optionally substituted by up to 2 identical or different substituents selected from hydroxyl, linear or branched alkoxy having up to 3 carbon atoms, phenyl, benzyloxy, phenoxy and pyridyl, it being possible for the rings in turn to be substituted by fluorine, chlorine, bromine, hydroxyl, cyano, linear or branched alkoxy having up to 3 carbon atoms, or a radical of the formula —(NH)$_a$—CONR[8]R[9], wherein R[8] and R[9] are identical or different and are hydrogen or linear or branched alkyl having up to 3 carbon atoms, and a is the number 0 or 1, or L is a radical of the formula —(CH$_2$)$_b$—T—(CH$_2$)$_c$, wherein b and c are identical or different and are the number 0, 1, 2, 3 or 4, and T is cyclopropyl, cyclobutyl, cyclopentyl, cyclohexyl, cycloheptyl, phenyl, pyridyl or piperidinyl which is optionally substituted by fluorine, chlorine, bromine, cyano, hydroxyl, carboxyl, linear or branched alkyl, alkoxycarbonyl or alkoxy, each of which has up to 5 carbon atoms, or a radical of the formula —CO—NH$_2$, R[1] and R[2] are identical or different and are hydrogen or linear or branched alkyl having up to 3 carbon atoms which is optionally substituted by hydroxyl, fluorine or a radical of the formula —NR[12]R[13], wherein R[12] and R[13] are identical or different and are hydrogen or linear or branched alkyl having up to 4 carbon atoms, or R[1], R[2] and L, together with the two nitrogen atoms, form a 1,4-diazacycloheptyl or [1,5]-diazoxanyl ring which is optionally substituted by hydroxyl, carboxyl, linear or branched acyl or alkoxycarbonyl, each of which has up to 4 carbon atoms, phenyl or linear or branched alkyl having up to 4 carbon atoms, which in turn can be substituted by hydroxyl, carboxyl, ureido, linear or branched alkoxy, acylamino or alkoxycarbonyl, each of which has up to 3 carbon atoms, or a group of the formula —(CO)$_d$—NR[14]R[15], wherein d is the number 0 or 1, and R[14] and R[15] are identical or different and are hydrogen or linear or branched alkyl having up to 3 carbon atoms, and/or the heterocycles are optionally substituted by a radical of the formula —(CO)$_e$—NR[16]R[17], wherein e is as defined above for d and is identical thereto or different therefrom, and R[16] and R[17] are identical or different and are as defined above for R[14] and R[15], or, in the case where b is the number 0 and c is as defined above, or c is the number 0 and b is as defined above, T and R[1] or, respectively, T and R[2], in each case together with the nitrogen atom, form a piperidine, pyrrolidine or 4-azatricyclo[5.2.2.0]-2,6-undecenyl ring, and R[3], R[4], R[5] and R[6] are identical or different and are hydrogen or linear or branched alkyl having up to 5 carbon atoms which is optionally substituted by hydroxyl, fluorine or a radical of the formula —NR[18]R[19], wherein R[18] and R[19] are identical or different and are as defined above for R[14] and R[15], or R[3] and R[4] and/or R[5] and R[6], in each case together with the nitrogen atom, form a morpholine, piperazinyl, piperidinyl or pyrrolidinyl ring, and their salts.

Very particularly preferred compounds of the general formula (I) are those in which R[1] and R[2] are hydrogen.

Processes for the preparation of the compounds of the general formula (I) according to the invention have also been found, said processes being characterized in that

[A] 2 equivalents of the compounds of the general formula (II)

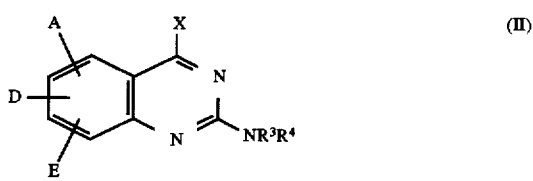

in which

A, D, E, R[3] and R[4] are as defined above, and

X is halogen, preferably chlorine, are reacted with diamines of the general formula (III)

in which

R[1], R[2] and L are as defined above, optionally in inert solvents and optionally in the presence of a base and/or an iodine salt, or

[B] 1 equivalent of the compound of the general formula (II) is reacted with the compounds of the general formula (III), under the conditions of process [A], to give compounds of the general formula (IV)

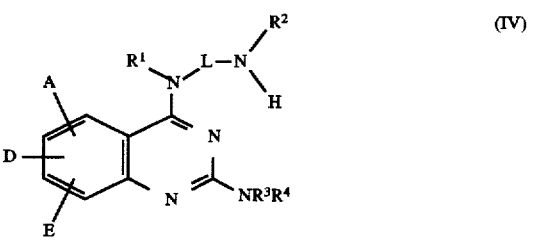

in which

R[1], R[2], A, D, E, R[3] and R[4] are as defined above, and these are then reacted with compounds of the general formula (IIa)

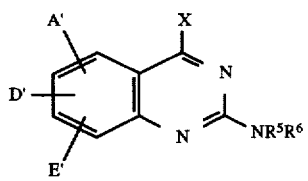

in which

A', D', E', $R^5$, $R^6$ and X are as defined above, under the conditions of process [A].

The process according to the invention can be exemplified by the following equation:

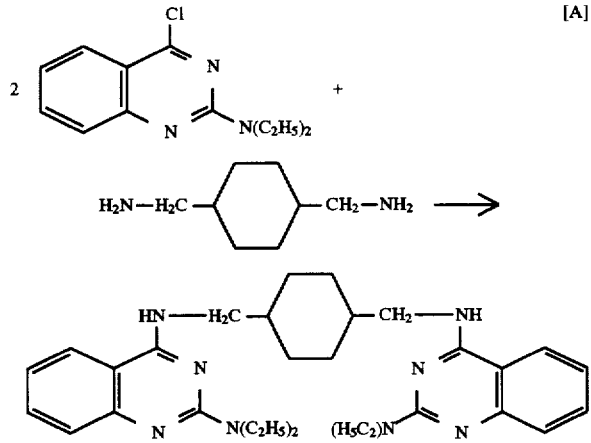

Suitable solvents are the conventional solvents which are not affected by the reaction conditions. These preferably include alcohols such as methanol, ethanol, propanol, isopropanol, hexanol, octanol or phenol, ethers such as diethyl ether, dioxane, tetrahydrofuran, glycol dimethyl ether or butyl methyl ether, ketones such as acetone or butanone, amides such as N-methylpyrrolidone, dimethylformamide or N-methylphosphorotriamide, dimethyl sulfoxide, acetonitrile, butyronitrile, ethyl acetate, halogenated hydrocarbons such as methylene chloride, chloroform or carbon tetrachloride, pyridine, picoline or N-methylpiperidine. It is also possible to use mixtures of said solvents. Tetrahydrofuran, butyronitrile, phenol and N-methylpyrrolidone are preferred. The reaction can also be carried out without a solvent.

Suitable bases are the conventional inorganic or organic bases. These preferably include alkali metal carbonates such as sodium or potassium carbonate, or organic amines such as diethylamine, triethylamine, tripropylamine, pyridine, picoline, N-methylpiperidine, lutidine or diisopropylethylamine. Diisopropylethylamine and tripropylamine are preferred.

Suitable iodine salts are alkali metal iodides such as lithium iodide, sodium iodide, potassium iodide and caesium iodide, and tetralkylammonium iodides such as benzyltributylammonium iodide. It is preferable to use sodium iodide and potassium iodide.

The iodine salts are generally used in an amount of 0.001 to 1 mol, based on 1 mol of the compounds of the general formula (II).

The base is used here in an amount of 1 to 5 mol, preferably of 1 to 2 mol, based on 1 mol of the compounds of the general formula (II).

The reactions are generally carried out in the temperature range between −20° C. and the reflux temperature of the solvent, preferably between +20° C. and the reflux temperature of the solvent.

The reaction can be carried out at normal, elevated or reduced pressure (e.g. 0.5 to 5 bar). It is generally carried out at normal pressure.

Some of the compounds of the general formula (II) are known or they can be prepared by known methods, for example by refluxing the corresponding 1H,3H-quinazoline-2,4-diones with phosphorus oxychloride in the presence of triethylamine.

The compounds of the general formula (III) are known per se or can be prepared by conventional methods.

Some of the compounds of the general formulae (IV) and (IVa) are known or novel and they can be prepared as described above.

The compounds according to the invention possess a valuable pharmacological spectrum of action which could not be anticipated.

The compounds according to the invention are ligands for apamine-sensitive potassium channels. This can be shown by studying the affinity for apamine binding sites, e.g. in bovine cerebral membranes. The compounds according to the invention inhibit the ion flows through these channels, as can be shown by rubidium efflux experiments and with electrophysiological methods.

The compounds have a positive influence on learning and memory faculties, as demonstrated by their performance-enhancing action in typical learning and memory models like the water maze, the Morris maze, passive avoidance or reminiscence tests in automated Skinner boxes. They possess an antidepressant potential, as verified by their activity in the Porsolt rat swimming test.

The compounds according to the invention are also suitable for the treatment of myotonic dystrophy, alcoholism and other addiction diseases, sleep disturbances and bronchial asthma.

By virtue of their pharmacological properties, the compounds according to the invention can be used for the preparation of drugs for the treatment of degenerative diseases of the central nervous system, e.g. those occurring in cases of dementia (multi-infarct dementia, MID, primary degenerative dementia, PDD, presenile Alzheimer's disease, HIV dementia and other forms of dementia).

They are also suitable for the treatment of age-related cerebral faculty impairment, organic brain syndrome (OBS) and age-associated memory impairment (AAMI).

They are suitable for the treatment of depression.

1) Binding of $^{125}$I-apamine to bovine cerebral membrane

Calf brains were obtained from the local abattoir. The hippocampus was prepared on ice and a membrane suspension was made up by homogenization twice in buffer (100 mM Tris-HCl, KCl 5 mM, pH 7.4) and centrifugation at 43,000×g. In a total volume of 500 μl, the incubation mixture contained 200 μg of membrane protein, 30 pM $^{125}$I-apamine and test substances in the concentration range $1\times10^{-9}$ to $1\times10^{-4}$ M. The non-specific binding of $^{125}$I-apamine was determined in the presence of $1\times10^{-7}$ M unlabelled apamine.

After preincubation for 30 min at room temperature (test substances and membrane homogenate), the samples were placed on ice for 10 min before the radioligand was added. The main incubation time was 60 min on ice. When the reaction time had elapsed, an excess of ice-cooled incubation buffer was added to each sample and the mixture was filtered with suction through cellulose acetate/nitrate membrane filters. The amount of bound $^{125}$I-apamine was measured with a gamma counter.

TABLE A:

| Ex. no. | $K_i$ |
|---|---|
| 1 | 0.16 μM |
| 2 | 0.008 μM |

2) Non-radioactive $Rb^+$ efflux assay for the identification of potassium channel modulators The potassium in PC12 cells is exchanged with rubidium, which is not present in the cells. This exchange is performed by incubating the cells over a period of 4 h in a physiological buffer containing 5.4 mM RbCl without KCl. This rubidium subsequently serves as a tracer for potassium.

The cells laden with $Rb^+$ in this way are washed three times and then stimulated by depolarization with 50 mM KCl to open potassium channels (10 min), causing $Rb^+$ to flow out of the cells into the supernatant according to the concentration gradient.

The rubidium contents in the cell supernatant and in the residual cells after they have been lysed with 1% Triton X-100 are then determined by means of atomic absorption spectroscopy. The relative proportion of rubidium in the cell supernatant (=$Rb^+$ efflux) is used as a measure of the potassium channel activity.

The effect of substances on the channel activity is measured by co-incubating, the test substance over the ten-minute stimulation period and determining its effect on the $Rb^+$ efflux in the manner described above.

TABLE B:

| Example no. | % Inhibition of the Rb efflux at a test concentration of 10 μM |
|---|---|
| 1 | 80 |
| 3 | 81 |

3) Morris maze

Subjects

Male ICR mice, 6–8 wks old and approx. 22–28 gm, were obtained from Harlan Sprague-Dawley, Inc. (Indianapolis, Ind.) and housed 8/cage with ad libitum access to food and water.

Water Maze Apparatus

The behavioral apparatus consisted of a circular galvanized steel tank painted white with a diameter of 76 cm and divided into four equally spaced quadrants, each containing a plastic fitting that allowed for the placement of an escape platform. Prior to the start of the behavioral testin,, the maze was filled daily to a depth of 1 cm above the escape platform (25 cm deep), maintained at a temperature of approx. 22° C., and was made opaque by the addition of 0.9 kg of powdered milk. Numerous stationary visual cues were present in the testing room. The data were recorded with the Multiple Zone Distance Traveled program of the Video-V analysis system (Columbus Instruments International Corp., Columbus, Ohio).

Modified Mouse Morris Water Maze Protocol

After a 1 week acclimation to the animal facility, the mice were given a 90 sec free swim, during which no escape platform was present. One to three days later, acquisition training began and consisted of 4 trials on each day for a total of three days (12 total trials), during which no drugs were given. The mice were randomly assigned a goal quadrant in which the escape platform was located. Animals were then placed in the maze (facing away from the center) at one of four equally spaced positions around the perimeter of the maze. The starting position varied for each mouse until they had started from each of the four positions once daily. On each of the training trials, the mice were allowed 120 sec to find the goal platform. If they failed to do so within the allotted time, they were placed on the platform. The intertrial interval was 30 sec during which time the mouse remained on the platform. On the fourth day, the mice were given a single 30 sec probe trial in which no escape platform was present. Thirty min or 1 hr prior to the start of the probe trial, mice were randomly assigned to groups that were given either drug or vehicle, and the time spent in each quadrant was measured.

The present invention also includes pharmaceutical formulations which contain one or more compounds of the general formula (I) together with inert, non-toxic, pharmaceutically appropriate adjuncts and excipients, or which consist of one or more active substances of the formula (I), as well as processes for the preparation of these formulations.

The active substances of the formula (I) should be present in these formulations in a concentration of 0.1 to 99.5% by weight, preferably of 0.5 to 95% by weight of the total mixture.

In addition to the active substances of the formula (I), the pharmaceutical formulations can also contain other pharmaceutical active substances.

The pharmaceutical formulations mentioned above can be prepared in conventional manner by known methods, for example with one or more adjuncts or excipients.

To achieve the desired result, it has generally proved advantageous to administer the active substance or substances of the formula (I) in total amounts of about 0.01 to about 100 mg/kg, preferably in total amounts of about 0.01 mg/kg to 10 mg/kg of body weight per 24 hours, optionally in the form of several individual doses.

However, it may be advantageous to deviate from said amounts, depending on the nature and body weight of the subject treated, the individual response to the drug, the nature and severity of the disease, the type of formulation and administration and the time or interval at which the drug is administered.

Starting compounds

Example I

4-Chloro-2-diethylaminoquinazoline

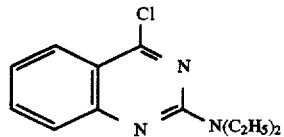

20.0 g of 1H,3H-quinazoline-2,4-dione were dissolved in 280 ml of phosphorus oxychloride, and 60 ml of triethylamine were added. After refluxing for 75 minutes, the excess phosphorus oxychloride was distilled off under vacuum and the residue was taken up slowly with 200 ml of ice-cold 1N sodium hydroxide solution. Extraction with dichloromethane (three times 150 ml), washing of the organic phase with water (three times 100 ml), drying over magnesium sulfate and distillation of the solvent on a rotary evaporator gave a brown oil, which could be used in the next reaction without further purification.

Yield: 17.7 g (60%)

Preparatory Examples

Example 1

1,3-Bis-[(2-diethylamino-4-quinazolyl)-aminomethyl]-cyclohexane (cis/trans isomeric mixture)

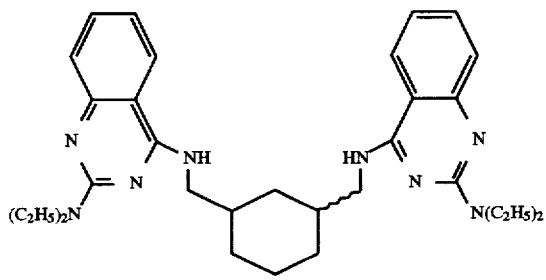

2.36 g of 4-chloro-2-diethylaminoquinazoline and 710 mg of 1,3-bis-(aminomethyl)cyclohexane (cis/trans isomeric mixture) were suspended in 50 ml of butyronitrile, and 1.74 ml of diisopropylethylamine were added. After refluxing for 16 hours and cooling to room temperature, the solution was treated with 50 ml of 1N sodium hydroxide solution and 100 ml of dichloromethane. The organic phase was washed with water until the washings were neutral, dried over magnesium sulfate and concentrated to dryness. The crude product could be purified by extraction of the residue by stirring with TBME (tert-butyl methyl ether).

Yield: 1.36 g (50%)

M.p.: 193° C.

MS-EI: 540 (67, M), 511 (100), 342 (52), 270 (38), 241 (35), 217 (47).

Example 2

1,5-Bis-[(2-diethylamino)-4-quinazolyl)amino]pentane

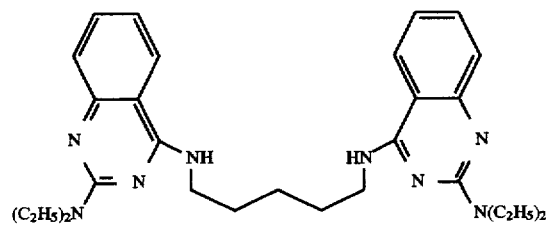

The title compound was prepared analogously to the instructions in Example 1 from 2.36 g of 4-chloro-2-diethylaminoquinazoline, 510 mg of 1,5-diaminopentane, 50 ml of butyronitrile and 1.74 ml of diisopropylethylamine.

Yield: 930 mg (37%)

M.p.: 172° C.

Synthesis of bis-[N-(4-quinazolyl)]-diamines 10.0 mmol of 4-chloro-2-diethylaminoquinazoline (Example I) were dissolved in 50 ml of tetrahydrofuran, 2.5 mmol of diamine were added and the mixture was refluxed for 4.5 h. After cooling to room temperature, it was concentrated to dryness on a rotary evaporator and the residue was chromatographed on silica gel 60 (Merck, 63–200 μm) with dichloromethane/methanol/acetic acid 60/40/25.

The compounds listed in Table 1 are prepared according to the general instructions indicated above or analogously to the instructions in Example 1.

TABLE 1

| Ex. No. | L | $R^1$ | $R^2$ | mp. (°C.) $R_f$ - value |
|---|---|---|---|---|
| 3 | —(CH$_2$)$_3$— | H | H | (A) |
| 4 | —(CH$_2$)$_6$— | H | H | (B) |
| 5 |  | | | 126° C. |

(A): MS: 472
(B): MS: 514

We claim:

1. 4,4'-Bridged bis-2,4-diaminoquinazolines of the general formula (I)

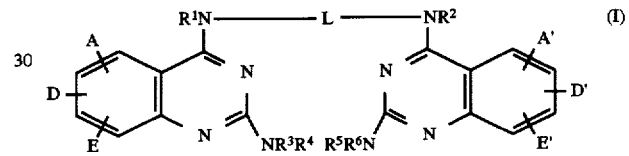

in which

A, A', D, D', E and E' are identical or different and are hydrogen, halogen, hydroxyl, nitro, trifluoromethyl, trifluoromethoxy or linear or branched alkyl or alkoxy, each of which has up to 6 carbon atoms, L is a linear or branched alkylene chain having 1 to 20 carbon atoms which is optionally interrupted by an oxygen or sulfur atom or by a group of the formula —NR$^7$, wherein R$^7$ is hydrogen or linear or branched alkyl having up to 4 carbon atoms, and where the alkylene chain is optionally substituted by up to 3 identical or different substituents selected from hydroxyl, linear or branched alkoxy having up to 5 carbon atoms, aryl or aralkoxy, each of which has up to 10 carbon atoms, and a 5- to 7-membered aromatic, optionally benzo-fused heterocycle having up to 3 heteroatoms from the group comprising S, N and/or O, it being possible for the rings in turn to be substituted by halogen, hydroxyl, cyano, linear or branched alkoxy having up to 6 carbon atoms, or a radical of the formula —(NH)$_a$—CONR$^8$R$^9$, wherein R$^8$ and R$^9$ are identical or different and are hydrogen or linear or branched alkyl having up to 6 carbon atoms, and a is the number 0 or 1, or L is a radical of the formula —(CH$_2$)$_b$—T—(CH$_2$)$_c$, wherein b and c are identical or different and are the number 0, 1, 2, 3, 4 or 5, and T is cycloalkyl having 3 to 6 carbon atoms, aryl having 6 to 10 carbon atoms or a 3- to 8-membered, saturated or unsaturated, optionally benzo-fused and/or heterocyclically or carbocyclically bridged heterocycle having up to 3 heteroatoms from the group comprising S, N and/or O, wherein all the ring systems are optionally substituted by up to 3 identical or different substituents selected from halogen, cyano, hydroxyl, nitro, carboxyl, linear or branched alkyl, alkoxycarbonyl or alkoxy, each of which has up to 9 carbon atoms, and a radical of the formula —CO—NR$^{10}$R$^{11}$, wherein R$^{10}$ and R$^{11}$ are as defined above for R$^8$ and R$^9$ and are identical thereto or different therefrom, R$^1$ and R$^2$ are identical or different and are hydrogen, phenyl or linear or branched alkyl having up to 6 carbon atoms which is optionally substituted by hydroxyl, halogen or a radical of the formula —NR$^{12}$R$^{13}$, wherein R$^{12}$ and R$^{13}$ are identical or different and are as defined above for R$^8$ and R$^9$, or R$^1$, R$^2$ and L, together with the two nitrogen atoms, form a 5- to 8-membered, saturated, partially unsaturated or aromatic heterocycle which is optionally benzo-fused and/or substituted by hydroxyl, carboxyl, linear or branched acyl or alkoxycarbonyl, each of which has up to 6 carbon atoms, phenyl or linear or branched alkyl having up to 6 carbon atoms, which in turn is substituted by hydroxyl, carboxyl, ureido, linear or branched alkoxy, acylamino or alkoxycarbonyl, each of which has up to 5 carbon atoms, or a group of the formula —(CO)$_d$—NR$^{14}$R$^{15}$, wherein d is the number 0 or 1, and R$^{14}$ and R$^{15}$ are identical or different and are as defined above for R$^8$ and R$^9$, and/or the heterocycle is optionally substituted by a radical of the formula —(CO)$_e$—NR$^{16}$R$^{17}$, wherein e is as defined above for d and is identical thereto or different therefrom, and R$^{16}$ and R$^{17}$ are identical or different and are as defined above for R$^8$ and R$^9$, or, in the case where b is the number 0 and c is as defined above, or c is the number 0 and b is as defined above, T and R$^1$ or, respectively, T and R$^2$, in each case together with the nitrogen atom, form a 3- to 8-membered, optionally benzo-fused and/or heterocyclically or carbocyclically bridged, saturated heterocycle having up to 2 heteroatoms from the group comprising S, N and/or O, and R$^3$, R$^4$, R$^5$ and R$^6$ are identical or different and are hydrogen, phenyl or linear or branched alkyl having up to 8 carbon atoms which is optionally substituted by hydroxyl, halogen or a radical of the formula —NR$^{18}$R$^{19}$, wherein R$^{18}$ and R$^{19}$ are identical or different and are as defined above for R$^8$ and R$^9$, or R$^3$ and R$^4$ and/or R$^5$ and R$^6$, in each case together with the nitrogen atom, form a 5- to 7-membered saturated heterocycle which can optionally contain up to 2 further heteroatoms from the group comprising S and O, or a radical of the formula —NR$^{20}$, wherein R$^{20}$ is as defined above for R$^7$ and is identical thereto or different therefrom, and their salts.

2. 4,4'-Bridged bis-2,4-diaminoquinazolines of the formula as claimed in claim 1 in which A, A', D, D', E and E' are identical or different and are hydrogen, fluorine, chlorine, bromine, hydroxyl, nitro, trifluoromethyl, trifluoromethoxy or linear or branched alkyl or alkoxy, each of which has up to 4 carbon atoms, L is a linear or branched alkylene chain having up to 15 carbon atoms which is optionally interrupted by an oxygen or sulfur atom or by a group of the formula —NR$^7$, wherein R$^7$ is hydrogen or linear or branched alkyl having up to 3 carbon atoms, and where the alkylene chain is optionally substituted by up to 2 identical or different substituents selected from hydroxyl, linear or branched alkoxy having up to 4 carbon atoms, phenyl, benzyloxy, phenoxy, pyridyl, pyrimidyl, pyridazinyl, quinolyl and isoquinolyl, it being possible for the rings in turn to be substituted by fluorine, chlorine, bromine, hydroxyl, cyano, linear or branched alkoxy having up to 4 carbon atoms, or a radical of the formula —(NH)$_a$—CONR$^8$R$^9$, wherein R$^8$ and R$^9$ are identical or different and are hydrogen or linear or branched alkyl having up to 4 carbon atoms, and a is the number 0 or 1, or a radical of the formula —(CH$_2$)$_b$—T—(CH$_2$)$_c$, wherein b and c are identical or different and are the number 0, 1, 2, 3 or 4, and T is cyclopropyl, cyclobutyl, cyclopentyl, cyclohexyl, cycloheptyl, phenyl, naphthyl, pyridyl, quinolyl, isoquinolyl, morpholinyl or piperidinyl which is optionally substituted by up to 2 identical or different substituents selected from fluorine, chlorine, bromine, cyano, hydroxyl, carboxyl, linear or branched alkyl, alkoxycarbonyl or alkoxy, each of which has up to 7 carbon atoms, and a radical of the formula —CO—NH$_2$, R$^1$ and R$^2$ are identical or different and are hydrogen or linear or branched alkyl having up to 3 carbon atoms which is optionally substituted by hydroxyl, fluorine or a radical of the formula —NR$^{12}$R$^{13}$, wherein R$^{12}$ and R$^{13}$ are identical or different and are hydrogen or linear or branched alkyl having up to 5 carbon atoms, or R$^1$, R$^2$ and L, together with the two nitrogen atoms, form a piperazinyl, 1,4-diazacycloheptyl or [1,5]-diazoxanyl ring which is optionally substituted by hydroxyl, carboxyl, linear or branched acyl or alkoxycarbonyl, each of which has up to 5 carbon atoms, phenyl or linear or branched alkyl having up to 5 carbon atoms, which can in turn be substituted by hydroxyl, carboxyl, ureido, linear or branched alkoxy, acylamino or alkoxycarbonyl, each of which has up to 4 carbon atoms, or a group of the formula $-(CO)_d-NR^{14}R^{15}$, wherein d is the number 0 or 1, and $R^{14}$ and $R^{15}$ are identical or different and are hydrogen or linear or branched alkyl having up to 4 carbon atoms, and/or the heterocycles are optionally substituted by a radical of the formula $-(CO)_e-NR^{16}R^{17}$, wherein e is as defined above for d and is identical thereto or different therefrom, and $R^{16}$ and $R^{17}$ are identical or different and are as defined above for $R^{14}$ and $R^{15}$, or, in the case where b is the number 0 and c is as defined above, or c is the number 0 and b is as defined above, T and $R^1$ or, respectively, T and $R^2$, in each case together with the nitrogen atom, form a piperidine, morpholine, pyrrolidine or 4-azatricyclo[5.2.2.0]-2,6-undecenyl ring, and $R^3$, $R^4$, $R^5$ and $R^6$ are identical or different and are hydrogen or linear or branched alkyl having up to 7 carbon atoms which is optionally substituted by hydroxyl, fluorine or a radical of the formula $-NR^{18}R^{19}$, wherein $R^{18}$ and $R^{19}$ are identical or different and are as defined above for $R^{14}$ and $R^{15}$, or $R^3$ and $R^4$ and/or $R^5$ and $R^6$, in each case together with the nitrogen atom, form a morpholine, piperazinyl, piperidinyl or pyrrolidinyl ring, and their salts.

3. A composition for treating diseases of the central nervous system comprising 4,4'-bridged bis-2,4-diaminoquinazolines as claimed in claim 1 and a biocompatible formulation aid.

4. A method of treating diseases of the central nervous system wherein said diseases are treatable by blocking the apamin-sensitive potassium channels, which comprises administering an effective amount of a compound according to claim 1 to a host in need thereof.

5. The method according to claim 4 wherein said disease is dementia.

6. The method according to claim 4 wherein said disease is depression.

7. The method according to claim 4 wherein said disease is myotonic dystrophy.

* * * * *